(12) United States Patent
Nair et al.

(10) Patent No.: US 6,670,186 B1
(45) Date of Patent: *Dec. 30, 2003

(54) RNA-LOADED ANTIGEN PRESENTING CELLS

(75) Inventors: Smita K. Nair, Durham, NC (US); David J. Boczkowski, Durham, NC (US); Eli Gilboa, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/667,319

(22) Filed: Sep. 22, 2000

Related U.S. Application Data

(60) Division of application No. 09/302,329, filed on Apr. 30, 1999, now Pat. No. 6,387,701, which is a continuation-in-part of application No. 09/073,819, filed on May 6, 1998, now Pat. No. 6,306,388, which is a continuation of application No. 08/640,444, filed on Apr. 30, 1996, now Pat. No. 5,853,719, said application No. 09/302,329, is a continuation-in-part of application No. 09/171,916, filed as application No. PCT/US97/07317 on Apr. 30, 1997.

(51) Int. Cl.[7] .......................... C12N 15/09; C12N 15/85
(52) U.S. Cl. .......................... 435/455; 435/325; 435/7.1
(58) Field of Search ....................... 424/93.21; 435/325, 435/355

(56) References Cited

U.S. PATENT DOCUMENTS

| | | | |
|---|---|---|---|
| 4,918,164 | A | 4/1990 | Hellstrom et al. |
| 5,662,907 | A | 9/1997 | Kubo et al. |
| 5,827,642 | A | 10/1998 | Riddell et al. |
| 5,831,068 | A | 11/1998 | Nair et al. |
| 5,853,719 | A | 12/1998 | Nair et al. |
| 6,130,087 | A | 10/2000 | Srivastava et al. |
| 6,306,388 | B1 | 10/2001 | Nair et al. |

FOREIGN PATENT DOCUMENTS

| | | |
|---|---|---|
| WO | WO 94/04171 | 3/1994 |
| WO | WO 94/04557 | 3/1994 |
| WO | WO 97/41210 | 11/1997 |

OTHER PUBLICATIONS

Kormanec et al., Isolation of total RNA from yeast and bacteria and detection of rRNA in northern blots. Biotechniques, (1994 Nov) 17 (5) 838–42.*

Porter et al., A rapid membrane–based viral RNA isolation method for the polymerase of chain reaction. Nucleic Acids Research, (Jul. 25, 1991) 19 (14) 4011.*

Crusinberry et al, "Immunotherapy of Renal Cell Cancer", Seminars in Surgical Oncology 7:221–229 (1991).

Rosenberg et al, "Use of Tumor–Infiltrating Lymphocytes and Interleukin–2 in the Immunotherapy of Patients With Metastatic Melanoma", The New England Journal of Medicine 319(25):1676–1680 (1998).

Donis–Keller, H., "Site specific enzymatic cleavage of RNA", Nucleic Acids Research 7(1):179–192 (1979).

Friedman, H., "Discussion Paper: Protective Immunity in Leukemic Mice Treated with Specific "Immunogenic" RNA", Annals New York Academy of Sciences 277(00):708–715 (1976).

Greenup et al, "Anti–Tumor Cytotoxicity of Poly(A)–Containing Messenger RNA Isolated From Tumour–Specific Immunogenic RNA", Br. J. Cancer 38:55–63 (1978).

Aarons et al, "Immune RNA Therapy as an Effective Adjuvant Immunotherapy After Surgery: An Animal Model", Journal of Surgical Oncology 23:21–26 (1983).

Porgador et al, "Combined Vaccination with Major Histocompatibility Class I and Interleukin 2 Gene–transduced Melanoma Cells Synergizes the Cure of Postsurgical Established Lung Metastases", Cancer Research 55:4941–4949 (1995).

Rötzschke et al, "Exact prediction of a natural T cell epitope", Eur. J. Immunol. 21:2891–2894 (1991).

van den Bosch et al, "T–Cell–Independent Macrophase Activation in Mice Induced with rRNA from *Listeria monocytogenes* and Dimethyldioctadecylammonium Bromide", Infection and Immunity 53(3):611–615 (1986).

Boon et al, "Human Tumor Antigens Recognized by T Lymphocytes", J. Exp. Med. 183:725–729 (1996).

Rifkind et al, "Delayed Hypertensitivity to Fungal Antigens in Mice. II. Molecular Classes in Immunogenic RNA Extracts that Transfer Delayed Hypersensitivity", The Journal of Infectious Diseases 133(5):523–532 (1976).

Rifkind et al, "Delayed Hypersensity to Fungal Antigens in Mice. III. Characterization of the Active Component in Immunogenic RNA Extracts", The Journal of Infectious Diseases 133(5):533–537 (1976).

Nair et al, "Cells Treated with TAP–2 Antisense Oligonucleotides Are Potent Antigen–Presenting Cells In Vitro and In Vivo", The Journal of Immunology 156:1772–1780 (1996).

Inada et al, "Comparison of the Ability of Lactate Dehydrogenase–Elevating Virus and Its Virion RNA T Infect Murine Leukemia Virus–Infected or –Uninfected Cell Lines", Journal of Virology 67(9):5698–5703 (1993).

Duke et al, "In Vitro Induction of Antibody Formation With Immunogenic RNA", Annals New York Academy of Sciences 207:145–159 (1973).

Garvey et al, "Characterization of RNA–Antigen Complexes", Annals New York Academy of Sciences 207:258–278 (1973).

(List continued on next page.)

Primary Examiner—Micahel Wilson
(74) Attorney, Agent, or Firm—Nixon & Vanderhye P.C.

(57) ABSTRACT

The present invention relates, in general, to RNA-loaded antigen presenting cells and, in particular, to methods for treating or preventing tumor formation or pathogen infection in a patient. The invention further relates to methods of monitoring T-cell stimulation and to methods of antigen discovery.

14 Claims, 8 Drawing Sheets

OTHER PUBLICATIONS

Dodd et al, "Immunogenic RNA in the Immunotherapy of Cancer: The Transfer of Antitumor Cytotoxic Activity and Tuberculin Sensitivity to Human Lymphocytes Using Xenogeneic Ribonucleic Acid", Annals New York Academy of Sciences 207:454–467 (1973).

Walker et al, "Cationic lipids direct a viral glycoproteion into the class I major histocompatibility complex antigen-presentation pathway", Proc. Natl. Acad. Sci. USA 89:7915–7918 (1992).

Vyas et al, "Specific Immunotherapy Proposed for Hepatitis B Virus Infection", Develop. biol. Standard. 30:350–356 (1975).

Wu et al, "Engineering an intracellular pathway for major histocompatibility complex class II presentation of antigens", Proc. Natl. Acad. Sci. USA 92:11671–11675 (1995).

Lin et al, "Treatment of Established Tumors with a Novel Vaccine That Enhances Major Histocompatibility Class II Presentation of Tumor Antigen", Cancer Research 56:21–26 (1996).

Bhoopalam et al, "Surface Immunoglobulins of Circulating Lymphocytes in Mouse Plasmacytoma. II. The Influence of Plasmacytoma RNA on Surface Immunoglobulins of Lymphocytes", Blood 39(4):465–471 (1972).

Kim et al, "Interleukin–2–secreting Mouse Fibroblasts Transfected with genomic DNA from Murine Melanoma Cells Prolong the Survival of Mice with Melanoma", Cancer Research 54:2531–2535 (1994).

Rouse et al, "Induction In Vitro of Primary Cytotoxic T–Lymphocyte Responses with DNA Encoding Herpes Simplex Virus Proteins", Journal of Virology 68(9):5685–5689 (1994).

Riddell et al, "Class 1 MHC–Restricted Cytotoxic T Lymphocyte Recognition of Cells Infected With Human Cytomegalovirus Does Not Require Endogenous Viral Gene Expression", The Journal of Immunology 146(8):2795–2804 (1991).

Boczkowski et al, "Dendritic Cells Pulsed wityh RNA are Potent Antigen–Presenting Cells In Vitro and In Vivo", J. Exp. Med. 284:465–472 (1996).

Rabinovich et al, "Vaccine Technologies: View to the Future", Science 265:1401–1404 (1994).

Morel et al, "Does preventive vaccination with engineered tumor cells work in cancer–prone transgenic mice?", Cancer Gene Therapy 5(2):92–100 (1998).

Gomez–Navarro et al, "Gene Therapy for Cancer", European Journal of Cancer 35(6):867–885 (1999).

Sprent et al, "Lymphocyte Life–Span and Memory", Science 265:1395–1399 (1994).

Oldstone et al, "How Viruses Escape from Cytotoxic T Lymphocytes: Molecular Parameters and Players", Virology 234:179–185 (1997) Article No. VY978674.

Pardoll, "Cancer Vaccines", Nature Medicine Vaccine Supplement 4(5):525–531 (1998).

Cohen et al, "Bumps on the Vaccine Road", Science 265:1371 (1994).

Gura, "Cancer Models", Systems for Identifying New Drugs Are Often Faulty, Science 278:1041–1042 (1997).

Villarreal et al, "History and Biological Strategy of Polyomavirus, Adenovirus, and Papillomavirus", Common Mechanisms of Transformation by Small DNA Tumor Viruses, Washington, D.C.: American Society of Microbiology, Chapter 1, pp. 1–17 (1989).

Machado et al, "Dialyzable transfer factor in experimental Chagas' disease: in vitro studies", Trop. Med. Parasit. 37:399–402 (1986).

Slomsky et al, "Induction of Antibody Synthesis In Vitro By Immunogenic RNA", Annals Med. Sect. Pol. Acad. Sci. 20(4):255–268 (1975).

* cited by examiner

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Endoplasmic
      reticulum retention peptide

<400> SEQUENCE: 1

Lys Asp Glu Leu
  1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Lysosome
      targeting peptide

<400> SEQUENCE: 2

Lys Phe Glu Arg Gln
  1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Lysosome
      targeting peptide

<400> SEQUENCE: 3

Gln Arg Glu Lys
  1

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Signal
      peptide of MHC Class II(
```

```
<400> SEQUENCE: 4

Met Ala Ile Ser Gly Val Pro Val Leu Gly Phe Phe Ile Ile Ala Val
 1               5                  10                  15

Leu Met Ser Ala Gln Glu Ser Trp Ala
            20                  25

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 5 cagttttca aagttgatta tact                                         24

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: CTL
      epitope

<400> SEQUENCE: 6

Ser Ile Ile Asn Phe Glu Lys Leu
 1               5

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 7
tcatattagt tgaaactttt tgac                                        24
```

RNA-LOADED ANTIGEN PRESENTING CELLS

This is a divisional of application Ser. No. 09/302,329, filed Apr. 30, 1999, now U.S. Pat. No. 6,387,701 issued May 14, 2002, which is a continuation-in-part of Ser. No. 09/073, 819, filed May 6, 1998, now U.S. Pat. No. 6,306,388; which is a continuation of Ser. No. 08/640,444, filed Apr. 30, 1996, now U.S. Pat. No. 5,853,719; application Ser. No. 09/302, 329 also being a continuation-in-part of Ser. No. 09/171,916, filed Feb. 16, 1999, now pending; which is a 371 of PCT/US97/07317, filed Apr. 30, 1997 the entire content of which is hereby incorporated by reference in this application.

TECHNICAL FIELD

The present invention relates, in general, to RNA-loaded antigen presenting cells and, in particular, to methods for treating or preventing tumor formation or pathogen infection in a patient. The invention further relates to methods of monitoring T-cell stimulation and to methods of antigen discovery.

BACKGROUND OF THE INVENTION

Previously-described methods for treating cancers include the use of chemotherapeutics, radiation therapy, and selective surgery. The identification of a few tumor antigens has led to the development of cell-based therapies. These methods rely on first identifying a tumor antigen (i.e., a polypeptide that is expressed preferentially in tumor cells, relative to non-tumor cells). Several human tumor antigens have been isolated from melanoma patients, and identified and characterized (Boon and van der Bruggen, 1996, J. Exp. Med. 183: 725–729). These polypeptide antigens can be loaded onto antigen-presenting cells, and then be administered to patients in a method of immunotherapy (i.e., as a vaccine). Alternatively, the polypeptide-loaded antigen presenting cells can be used to stimulate CTL proliferation ex vivo. The stimulated CTL are then administered to the patient in a method of adoptive immunotherapy.

A variety of methods have been described for treating infections with intracellular pathogens such as viruses and bacteria. For example, antibiotics are commonly used to treat bacterial infections. Preparations of killed pathogens can also serve as vaccines. In addition, CTL-based therapies have been described for treating such infections.

SUMMARY OF THE INVENTION

It has now been discovered that tumor formation in a patient can be treated or prevented by administering to the patient an antigen-presenting cell(s) that is loaded with antigen encoded in RNA derived from a tumor. For convenience, an RNA-enriched tumor preparation can be used in lieu of purified RNA. The invention thus circumvents the need purify RNA or isolate and identify a tumor antigen. Using similar methods and pathogen-derived RNA, pathogen infection in a patient can be treated or prevented. The RNA-loaded antigen-presenting cells can be used to stimulate CTL proliferation ex vivo or in vivo. The ex vivo expanded CTL can be administered to a patient in a method of adoptive immunotherapy.

Accordingly, the invention features a method for producing an RNA-loaded antigen-presenting cell (APC); the method involves introducing into an APC in vitro (i) tumor-derived RNA that includes tumor-specific RNA which encodes a cell-surface tumor antigenic epitope which includes T cell proliferation or (ii) pathogen-derived RNA that includes pathogen-specific RNA which encodes a pathogen antigenic epitope that induces T cell proliferation. Upon introducing RNA into an APC (i.e., "loading" the APC with RNA), the RNA is translated within the APC, and the resulting protein is processed by the MHC class I or class II processing and presentation pathways. Presentation of RNA-encoded peptides begins the chain of events in which the immune system mounts a response to the presented peptides.

Preferably, the APC is a professional APC, such as a dendritic cell or a macrophage. Alternatively, any APC can be used. For example, endothelial cells and artificially generated APC can be used. The RNA that is loaded onto the APC can be provided to the APC as purified RNA, or as a fractionated preparation of a tumor or pathogen. The RNA can include poly $A^+$ RNA, which can be isolated by using conventional methods (e.g., use of poly dT chromatography). Both cytoplasmic and nuclear RNA are useful in the invention. Also useful in the invention is RNA encoding defined tumor or pathogen antigens or epitopes, and RNA "minigenes" (i.e., RNA sequences encoding defined epitopes). If desired, tumor specific or pathogen-specific RNA can be used; such RNA can be prepared using art known techniques such as subtractive hybridization against RNA from non-tumor cells or against related, but non-pathogenic, bacteria or viruses.

The RNA that is loaded onto APC can be isolated from a cell, or it can be produced by employing conventional molecular biology techniques. For example, RNA can be extracted from tumor cells, reverse transcribed into cDNA, which can be amplified by PCR, and the cDNA then is transcribed into RNA to be used in the invention. If desired, the cDNA can be cloned into a plasmid before it is used as a template for RNA synthesis. RNA that is synthesized in vitro can, of course, be synthesized partially or entirely with ribonucleotide analogues or derivatives. Such analogues and derivatives are well known in the art and can be used, for example, to produce nuclease-resistant RNAs. The use of RNA amplification techniques allows one to obtain large amounts of the RNA antigen from a small number of cells.

Included within the invention are methods in which the RNA is isolated from a frozen or fixed tissue. Tumor specimens commonly are isolated from cancer patients and then stored, for example, as cryostat or formalin fixed, paraffin-embedded tissue sections. Because cancer patients often have few tumor cells, the isolation of RNA from fixed tissues is particularly advantageous in producing the APC's of the invention because the method can utilize a small tissue sample. Microdissection techniques can be used to separate tumor cells from normal cells. RNA can then be isolated from the tumor cells and amplified in vitro (e.g., by PCR or reverse transcription PCR (RT-PCR)). The resulting, amplified RNA then can be used to produce the RNA-loaded APC's described herein.

If desired, RNA encoding an immunomodulator can also be introduced into the APC loaded with tumor-derived or pathogen-derived RNA. In this embodiment, the RNA-encoded immunomodulator is expressed in the APC and enhances the therapeutic effect (e.g., as a vaccines) of the RNA-loaded APC'S. Preferably, the immunomodulator is a cytokine or costimulatory factor (e.g., an interleukin, such as IL-1, IL-2, IL-3, IL-4, IL-5, IL-6, IL-7, IL-8, IL-9, IL-10, IL-11, IL-12, or IL-15, or GM-CSF).

To introduce RNA into an APC, the APC may be contacted with the tumor- or pathogen-derived RNA in the presence of a cationic lipid, such as DOTAP or 1:1 (w/w) DOTMA:DOPE (i.e., LIPOFECTIN). Alternatively, "naked" RNA can be introduced into the cells. Other art-known transfection methods also can be used to introduce the RNA into the APC.

In a variation of the above methods, the RNA that is introduced into the APC can be engineered such that it encodes a cell trafficking signal sequence in addition to a tumor antigen or pathogen antigen. Such an engineered RNA can be thought of as containing two RNA sequences that are covalently linked and which direct expression of a chimeric polypeptide. One RNA sequence encodes the tumor or pathogen antigen, while the other RNA sequence encodes the cell trafficking sequence, thus forming a chimeric polypeptide. The chimeric polypeptides that contain an antigen linked to a trafficking sequence are channeled into the MHC class II antigen presentation pathway. Examples of suitable trafficking sequences are provided below.

Because practicing the invention does not require identifying an antigen of the tumor cell or pathogen, RNA derived from essentially any type of tumor or pathogen is useful. For example, the invention is applicable, but not limited to, the development of therapeutics for treating melaomas, bladder cancers, breast cancers, pancreatic cancers, prostate cancers, colon cancers, and ovarian cancers. In addition, the invention can treat or prevent infections with pathogens such as Salonella, Shigella, Enterobacter, human immunodeficiency virus, Herpes virus, influenza virus, poliomyelitis virus, measles virus, mumps virus, or rubella virus.

The antigen-presenting cells produced in accordance with the invention can be used to induce CTL responses in vivo and ex vivo. Thus, the invention includes methods for treating or preventing tumor formation in a patient by administering to the patient a therapeutically effective amount of APC loaded with tumor-derived RNA. The tumor-derived RNA can be derived from the patient, e.g., as an RNA-enriched tumor preparation. Alternatively, the tumor-derived RNA used in such a treatment regimen can be derived from another patient afflicted with the same, or a similar, type of cancer. Likewise, APC loaded with pathogen-derived RNA can be used to treat or prevent a pathogen infection in a patient.

Included within the invention are methods for producing a cytotoxic T lymphocyte. Such a CTL can be produced by contacting a T lymphocyte in vitro with an antigen-presenting cell that is loaded with tumor-derived or pathogen-derived RNA, and maintaining the T lymphocyte under conditions conducive to CTL proliferation, thereby producing a CTL. The resulting CTL show remarkable specificity for the pathogen or the cells of the tumor from which the loaded. RNA is derived. Such CTL can be administered to a patient in a variation of conventional adoptive immunotherapy methods.

Also included within the invention are methods of monitoring patients for tumor-specific or pathogen-specific immune responses and thereby monitoring the effect of a particular vaccination strategy. In accordance with this method, APC's loaded with RNA derived from a patient's tumor or from an infection-producing pathogen can be substituted, for example, for cells of the tumor or pathogen or pathogen-infected cells in assays designed to detect the existence of tumor-specific or pathogen-specific T cells in the patient. This approach is advantageous as the availability of tumor cells or pathogen or pathogen-infected cells is limited whereas APC's can be generated from most patients and sufficient RNA can be obtained by amplification. APC's suitable for use in this method include dendritic cells, macrophages or fibroblasts. Preferred cells (e.g., dendritic cells and macrophages) express MHC class II molecules. The RNA-loaded APC's can be incubated with the patient's T cells (e.g., PBMC) and standard assays, including cytotoxicity assays, can be used to measure tumor-specific or pathogen-specific CTL levels. Such assays can be used to establish, for example, the efficacy of a strategy being used. To distinguish between CD8 and CD4 T cell responses, the corresponding subsets can be first separated using, for example, standard protocols. This method is not limited to the monitoring of patients treated in accordance with the therapeutic strategies described herein, and can, in fact, be used in patients not undergoing treatment.

In a variation of the above methods, the invention provides a method for generating a tumor-specific (or pathogen-specific) CTL response. Because most cancer patients naturally display a non-detectable or poor tumor-specific CTL response, this method is particularly useful since it provides a method for producing CTL response using antigens obtained from any patient.

The invention further includes method of identifying antigens that induce a T cell response, that is, a tumor-specific CD4 or CD8 cell response. In accordance with this method, RNA can be isolated from a patient's tumor, amplified, if necessary, using, for example, protocols as described herein, and introduced into APC's (for example, dendritic cells or macrophages). RNA-loaded APC's ("stimulator cells") are thus produced that present on the surface thereof an antigen encoded in the RNA. The stimulator cells can then be contacted with T cells of the patent so that T cells are produced that are sensitized to the displayed antigen. A cDNA expression library can be generated from the tumor-derived RNA and that library can be introduced into cultured cells of the patient so that individual cells of the culture are produced that express at least one DNA molecule of the library. The cultured cells can then be contacted with the sensitized T cells and the determination made, for example, using any of a variety of standard techniques (e.g., cytotoxicity assays), which of the cultured cells expresses an antigen recognized by the sensitized T cells. Cells that produce an antigen recognized by the sensitized T cells are cells that produce an antigen that elicits a T cell response directed against the tumor. To facilitate the identification of tumor specific antigens in accordance with this method, subtractive hybridization strategies can be used. That is, RNA derived from the tumor cells and from non-tumor cells can be used in a subtractive hybridization method to obtain tumor-specific RNA that can be introduced into APC's. Alternatively or additionally, tumor-derived RNA can be size-fractionated prior to introduction into APC's. Size-fractionation can be effected using standard protocols. While this antigen-identification method has been described in the context of tumor-specific antigens, it will be appreciated that the same approach can be used to identify pathogen-specific antigens by using APC's loaded with RNA isolated from the pathogen or pathogen-infected cells from the patient.

The invention also includes methods for treating or preventing tumor formation in a patient by administering to the patient a therapeutically effective amount of APC loaded with tumor-derived RNA. Similarly, the invention provides methods for treating pathogen infection in a patient by administering to the patient a therapeutically effective amount of APC loaded with pathogen-derived RNA. The T lymphocytes that are used in these various therapeutic methods can be derived from the patient to be treated, or haplotype-matched CTL from a donor can be used.

Similarly, the RNA used in these methods can be derived from the patient to be treated, or RNA from a donor can be used.

By "RNA-loaded" or "RNA-pulsed" antigen-presenting cell is meant an APC (e.g., a macrophage or dendritic cell) that was incubated or transfected with RNA, e.g., RNA derived from a tumor or pathogen. Such RNA can be loaded onto the APC by using conventional nucleic acid transfection methods, such as lipid-mediated transfection, electroporation, and calcium phosphate transfection. For example, RNA can be introduced into APC by incubating the APC with the RNA (or extract) for 1 to 24 hours (e.g., 2 hours) at 37° C., preferably in the presence of a cationic lipid.

By "tumor-derived" RNA is meant a sample of RNA that has its origin in a tumor cell, and which includes RNA corresponding to a tumor antigen(s). Included is RNA that encodes all or a portion of a previously identified tumor antigen. Similarly "pathogen-derived" RNA is a sample of RNA that has its origin in an pathogen (e.g., a bacterium or virus, including intracellular pathogens). Such RNA can be "in vitro transcribed," e.g., reverse transcribed to produce cDNA that can be amplified by PCR and subsequently be transcribed in vitro, with or without cloning the cDNA. Also included is RNA that is provided as a fractionated preparation of tumor cell or pathogen. Because even an unfractionated RNA preparation (e.g., total RNA or total poly $A^+$ RNA) can be used, it is not necessary that a tumor or pathogen antigen be identified. In one embodiment, the preparation is fractionated with respect to a non-RNA component(s) of the cell in order to decrease the concentration of a non-RNA component, such as protein, lipid, and/or DNA, and enrich the preparation for RNA. If desired, the preparation can be further fractionated with respect to the RNA (e.g., by subtractive hybridization) such that "tumor-specific" or "pathogen-specific" RNA is produced.

By "tumor-specific" RNA is meant an RNA sample that, relative to unfractionated tumor-derived RNA, has a high content of RNA that is preferentially present in a tumor cell compared with a non-tumor cell. For example, tumor-specific RNA includes RNA that is present in a tumor cell, but not present in a non-tumor cell. Also encompassed in this definition is an RNA sample that includes RNA that is present both in tumor and non-tumor cells, but is present at a higher level in tumor cells than in non-tumor cells. Also included within this definition is RNA that encodes a previously identified tumor antigen and which is produced in vitro, e.g., from a plasmid or by PCR. Alternatively, tumor-specific RNA can be prepared by fractionating an RNA sample such that the percentage of RNA corresponding to a tumor antigen is increased, relative to unfractionated tumor-derived RNA. For example, tumor-specific RNA can be prepared by fractionating tumor-derived RNA using conventional subtractive hybridization techniques against RNA from non-tumor cells. Likewise, "pathogen-specific" RNA refers to an RNA sample that, relative to unfractionated pathogen-derived RNA, has a high content of RNA that is preferentially present in the pathogen compared with a non-pathogenic strain of bacteria or virus.

By "trafficking sequence" is meant an amino acid sequence (or an RNA encoding an amino acid sequence) that functions to control intracellular trafficking (e.g., directed movement from organelle to organelle or to the cell surface) of a polypeptide to which it is attached.

The invention offers several advantages. Vaccinations performed in accordance with the invention circumvent the need to identify specific tumor rejection antigens or pathogen antigens, because the correct antigen(s) is automatically selected from the tumor- or pathogen-derived RNA when unfractionated RNA is used. If desired, the risk of generating an autoimmune response can be diminished by using tumor-specific RNA. In addition, vaccination with cells loaded with unfractionated tumor-derived RNA likely elicits immune responses to several tumor antigens, reducing the likelihood of "escape mutants." The invention also extends the use of active immunotherapy to treating cancers for which specific tumor antigens have not yet been identified, which is the vast majority of cancers. Furthermore, the RNA to be introduced into APC's can be derived from fixed tissue samples. Fixed samples of tumor tissues are routinely prepared in the course of diagnosing cancer; thus, the use of RNA from such samples does not require subjecting a patient to an additional invasive procedure. Because most cancer patients have low tumor burdens, the methods of the invention that involve isolation and amplification of RNA from fixed tumor tissues are particularly valuable. The invention can be used efficaciously even if the tumor itself displays poor immunogenicity. In addition, the invention is useful for reducing the size of preexisting tumors, including metastases even after removal of the primary tumor. Finally, the invention offers the advantage that antigen-presenting cells that are loaded with in vitro transcribed RNA can be more potent vaccines than are antigen-presenting cells that are loaded with peptide antigens.

DETAILED DESCRIPTION

Figure 1:
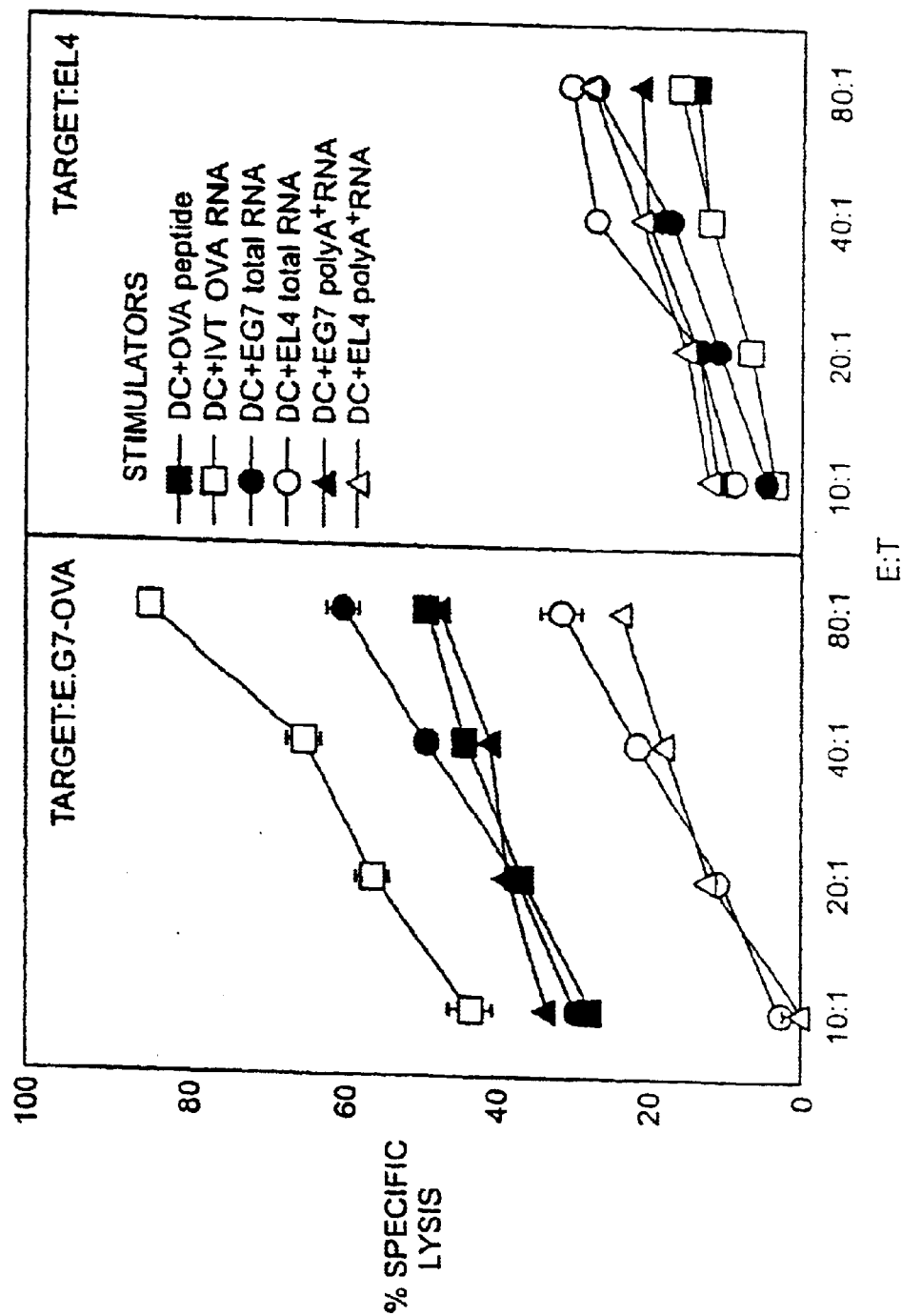
FIG. 1 is a graph illustrating primary OVA-specific CTL induction in vitro with dendritic cells pulsed with RNA. DC were pulsed with total RNA or polyA$^+$ RNA obtained from E.G7-OVA or 'EL4 cells, or in vitro transcribed OVA RNA in the presence of the cationic lipid DOTAP as described herein. DC pulsed with the OVA peptide were used for comparison. DC and naive T cells were incubated for 5 days at a R/S of 20:1. Viable lymphocytes were harvested, and the CTL activity was determined in a routine europium release assay. E.G7-OVA and EL4 cells were used as targets. This experiment was repeated three times with similar results.

Before providing detailed working examples of the invention, certain parameters of the invention will be described generally.

A variety of methods are suitable for producing the tumor- or pathogen-derived RNA that can be used in the invention. As the following examples illustrate, it is not necessary that the RNA be provided to the APC in a purified form. Preferably, the RNA sample (i.e., the fractionated tumor preparation or IVT RNA sample) is at least 50%, more preferably 75%, 90%, or even 99% RNA (wt/vol). In practicing the invention, antigen-presenting cells, preferably professional APC such as dendritic cells and macrophage, are used. Such cells can be isolated according to previously-described procedures.

Any of a variety of methods can be used to produce RNA-containing tumor preparations. For example, the tumor preparations can be produced by sonicating tumor cells in a mammalian cell culture medium such as Opti-MEM or a buffer such as phosphate buffered saline. Similarly, pathogen-derived RNA can be produced by sonicating pathogenic bacteria or cells containing a pathogenic virus. Other methods for disrupting cells also are suitable, provided that the method does not completely degrade the tumor- or pathogen-derived RNA. Typically, the RNA preparation has $10^6$ to $10^8$ cells/ml; most preferably $10^7$ cells/ml. As alternatives, or in addition, to sonication, the tumor- or pathogen-derived RNA can be prepared by employing conventional RNA purification methods, such as guanidinium isothiocyanate methods and/or oligo dT chromatography methods for isolating poly A+ RNA. IVT RNA, synthesized according to conventional methods, can be used in lieu of RNA in tumor preparations. For example, RNA from a tumor or pathogen can be reverse transcribed into cDNA, which then is amplified by conventional PCR techniques to provide an essentially unlimited supply of cDNA corresponding to the tumor or pathogen RNA antigen. Conventional in vitro transcription techniques and bacterial polymerases then are used to produce the IVT RNA. As an alternative, the IVT RNA can be synthesized from a cloned DNA sequence encoding a tumor or pathogen polypeptide antigen. Methods for identifying such antigens are known in the art; for example, several melanoma peptide antigens have been identified. RNA transcribed in vitro from cDNA encoding identified peptide antigens can serve as tumor- or pathogen-specific RNA in the invention. As an alternative, RNA can be transcribed from "minigenes" consisting of a portion of the tumor antigen cDNA that encodes an epitope. Tumor- or pathogen-specific RNA can also be produced by employing conventional techniques for subtractive hybridization. For example, an RNA sample from tumor cells and non-tumor cells can be used in the subtractive hybridization method to obtain tumor-specific RNA.

If desired, the tumor-derived or pathogen-derived RNA can be prepared from frozen or fixed tissues. Although not required, the tissue sample can be enriched for tumor-specific RNA. Microdissection techniques that are suitable for separating tumor cells from non-tumor cells have been described (Zhuang et al., 1995, Cancer Res. 55:467–471; Luqmani et al., 1992, Anal. Biochem. 200:291–295; Luqmani et al., 1994, Anal. Biochem. 222:102–109; Turbett et al., 1996, BioTech. 20:846–853). Once the tumor cells are separated from the non-tumor cells, tumor-derived RNA can be isolated from the tumor cells using art-known techniques. For example, tumor-derived poly-A+ RNA can be isolated by hybridizing the RNA to a solid phase, such as oligo(dT) linked to paramagnetic beads (see, e.g., Raineri et al., 1991, Nucl. Acids. Res. 19:4010). The first cDNA strand then is synthesized by reverse transcription, the RNA is removed, and the second strand is synthesized (e.g., with DNA polymerase). Conventional in vitro transcription methods then can be used to synthesize the RNA. Other art-known methods for amplifying RNA from a small number of cells, or even a single cell, also can be used in the invention.

An RNA molecule that encodes a tumor or pathogen antigenic epitope can, if desired, be engineered such that it also encodes a cell trafficking signal sequence. Such a chimeric RNA molecule can be produced using conventional molecular biology techniques. The chimeric RNA that is introduced into an APC encodes chimeric polypeptide, which contains an antigen linked to a trafficking sequence that directs the chimeric polypeptide into the MHC class II antigen presentation pathway. For example, the trafficking sequences employed in this embodiment of the invention may direct trafficking of the polypeptide to the endoplasmic reticulum (ER), a lysosome, or an endosome, and include signal peptides (the amino terminal sequences that direct proteins into the ER during translation), ER retention peptides such as KDEL (SEQ ID NO: 1); and lysosome-targeting peptides such as KFERQ (SEQ ID NO: 2), QREK (SEQ ID NO: 3), and other pentapeptides having Q flanked on one side by four residues selected from K, R, D, E, F, I, V, and L. A preferred signal peptide that can be used in the invention is the LAMP-1 sorting signal (Wu et al., 1995, Proc. Natl. Acad. Sci. 92:11671–11675; Lin et al., 1996, Cancer Research 56: 21–26). Another example of a signal peptide that is useful in the invention is a signal peptide substantially identical to that of an MHC subunit such as class II α or β; e.g., the signal peptide of MHC class II α is contained in the sequence MAISGVPVLGFFIIAVLM-SAQESWA (SEQ ID NO: 4). If desired, the signal peptide encoded by the RNA of the invention may include only a portion (typically at least ten amino acid residues) of the specified 25 residue sequence, provided that portion causes trafficking of the polypeptide to the ER.

Transfection methods that are suitable for introducing the tumor- or pathogen-derived RNA into an antigen-presenting cell are know in the art. For example, 5–50 μg of RNA in 500 μl of Opti-MEM can be mixed with a cationic lipid at a concentration of 10 to 100 μg, and incubated at room temperature for 20 to 30 minutes. Other suitable lipids include LIPOFECTIN™ (1:1 (w/w) DOTMA:DOPE), LIPOFECTAMINE™ (3:1 (w/w) DOSPA:DOPE), DODAC:DOPE (1:1), CHOL:DOPE (1:1), DMEDA, CHOL, DDAB, DMEDA, DODAC, DOPE, DORI, DORIE, DOSPA, DOTAP, and DOTMA. The resulting RNA-lipid complex is then added to $1-3\times10^6$ cells, preferably $2\times10^6$, antigen-presenting cells in a total volume of approximately 2 ml (e.g., in Opti-MEM), and incubated at 37° C. for 2 to 4 hours. Alternatively, the RNA can be introduced into the antigen presenting cells by employing conventional techniques, such as electroporation or calcium phosphate transfection with $15\times10^6$ cells and 5 to 50 μg of RNA. Typically, 5–20 μg of poly $A^+$ RNA or 25–50 μg of total RNA is used.

When the RNA is provided as a tumor or pathogen preparation, the preparation typically is fractionated or otherwise treated to decrease the concentration of proteins, lipids, and/or DNA in the preparation, and enrich the preparation for RNA. For example, art-known RNA purification methods can be used to at least partially purify the RNA from the tumor cell or pathogen. It is also acceptable to treat the RNA preparation with proteases or RNase-free DNases. Of course, the RNA can be synthesized using art-known nuclease-resistant analogues or derivatives in order to render the RNA less susceptible to ribonucleases.

If desired, RNA encoding an immunomodulator, such as a cytokine or a co-stimulatory factor, can be introduced into the RNA-loaded APC's of the invention. In this embodiment of invention, the RNA encoding the immunomodulator may be introduced into the APC prior to, simultaneously with, or subsequent to introduction of the tumor or pathogen-derived RNA. The methods described herein for introducing the tumor-derived or of pathogen-derived RNA into the APC also are suitable for introducing into the APC RNA encoding an immunomodulator (e.g., a cytokine or costimulatory factor). Sequences encoding numerous proteins are known in the art and can be used in the invention. If desired, RNA encoding two or more immunomodulators can be introduced into the APC. Typically, 5–20 μg of each RNA is introduced into the APC, as is described above for tumor- and pathogen-derived RNA.

The RNA-loaded antigen-presenting cells of the invention can be used to stimulate CTL proliferation in vivo or ex vivo. The ability of RNA-loaded antigen-presenting cells to stimulate a CTL response can be measured or detected by measuring or detecting T-cell activation, for example, in a conventional cytotoxicity assay. In examples provided below, the cytotoxicity assay entails assaying the ability of the effector cells to lyse target cells. If desired, the target cells can be RNA-loaded APC's produced in accordance with the invention (i.e., APC's that present an RNA-encoded cell surface tumor or pathogen antigenic epitope that induces T cell proliferation). As is described below, the commonly-used europium release assay can be used to assay CTL sensitization. Typically, $5-10\times10^6$ target cells are labeled with europium diethylenetriamine pentaacetate for 20 minutes at 4° C. After several washes, $10^4$ europium-labeled target cells and serial dilutions of effector cells at an effector:target ratio ranging from 50:1 to 6.25:1 are incubated in 200 μl RPMI 1640 with 10% heat-inactivated fetal calf serum in 96-well plates. The plates are centrifuged at 500×g for 3 minutes and the incubated at 37° C. in 5% $CO_2$ for 4 hours. A 50 μl aliquot of the supernatant is collected, and europium release is measured by time resolved fluorescence (Volgmann et al., J. Immunol. Methods 119:45–51, 1989).

In an alternative method for detecting CTL sensitization, an increase in cytokine secretion by the CTL is detected, relative to the level of cytokine secretion prior to contacting the CTL with an RNA-loaded APC. In situ hybridization assays, such as ELISPOT assays, can be used to detect secretion of cytokines such as TNF-α and/or γ-interferon.

The following working examples are meant to illustrate, not limit, the invention.

EXAMPLE 1

The following experimental details are relevant to the studies described below.
Mice
Seven to eight weeks old and retired breeder female C57BL/6 mice ($H-2^b$) were obtained from the Jackson Laboratory (Bar Harbor, Me.).
Cell Lines
The F10.9 clone of the B16 melanoma of C57BL/6 origin is a highly metastatic, poorly immunogenic, and low class I expressing cell line. F10.9/K1 is a poorly metastatic and highly immunogenic cell line derived by transfecting F10.9 cells with class I molecule, $H-2K^b$ cDNA. RMA and RMA-S cells are derived from the Rauscher leukemia virus-induced T cell lymphoma RBL-5 of C57BL/6 ($H-2^b$) origin. Other cell lines used were EL4 (C57BL/6, $H-2^b$, thymoma), E.G7-OVA (EL4 cells transfected with the cDNA of chicken ovalbumin (OVA)), A20($H-2^c$ B cell lymphoma) and L929 ($H-2^k$ fibroblasts). Cells were maintained in DMEM supplemented with 10% fetal calf serum (FCS), 25 mM Hepes, 2 mM L-glutamine and 1 mM sodium pyruvate. E.G7-OVA cells were maintained in medium supplemented with 400

μg/ml G418 (GIBCO, Grand Island, N.Y.) and F10.9/K1 cells were maintained in medium containing 800 μg/ml G418.

Antigen Presenting Cells and Responder T Cells

Splenocytes obtained from naive C57BL/6 female retired breeders were treated with ammonium chloride Tris buffer for 3 minutes at 37° C. to deplete red blood cells. Splenocytes (3 ml) at $2 \times 10^7$ cells/ml were layered over a 2 ml metrizamide gradient column (NyComed Pharma AS, Oslo, Norway; analytical grade, 14.5 g added to 100 ml PBS, pH 7.0) and centrifuged at 600 g for 10 minutes. The dendritic cell-enriched fraction from the interface was further enriched by adherence for 90 minutes. Adherent cells (mostly dendritic cells (DC) and a few contaminating macrophage (MØ) were retrieved by gentle scraping, and subjected to a second round of adherence at 37° C. for 90 minutes to deplete the contaminating MØ. Non-adherent cells were pooled as splenic DC and FACS analysis showed approximately 80%–85% DC (mAb 33D1), 1–2% MØ (mAb F4/80), 10% T cells, and <5% B Cells (data not shown).

The pellet was resuspended and enriched for MØ by two rounds of adherence at 37° C. for 90 minutes each. More than 80% of the adherent population was identified as MØ by FACS analysis, with 5% lymphocytes and <55% DC.

B cells were separated from the non-adherent population (B and T cells) by panning on anti-Ig coated plates. The separated cell population, which was comprised of >80% T lymphocytes by FACS analysis was used as responder T cells.

Isolation of Total and Poly $A^+$ Cellular RNA

Total RNA was isolated from actively growing tissue culture cells as previously described (Chomczynski and Sacchi, 1987, Anal. Biochem. 162: 156–159). Briefly, $10^7$ cells were lysed in 1 ml of guanidinium isothiocyanate (GT) buffer (4 M quanidinium isothiocyanate, 25 mM sodium citrate, pH 7.0; 0.5% sarcosyl, 20 mM EDTA, and 0.1 M 2-mercaptoethanol). Samples were vortexed, and followed by sequential addition of 100 μl 3 M sodium acetate, 1 ml water-saturated phenol and 200 μl chloroform:isoamyl alcohol (49:1). Suspensions were vortexed and then placed on ice for 15 minutes. The tubes were centrifuged at 10000xg, at 4° C. for 20 minutes, and the supernatant was carefully transferred to a fresh tube. An equal volume of isopropanol was added and the samples were placed at −20° C. for at least 1 hour. RNA was pelleted by centrifugation as above. The pellet was resuspended in 300 μl GT buffer, and then transferred to a microcentrifuge tube. RNA was again precipitated by adding an equal volume of isopropanol and placing the tube at −20° C. for at least 1 hour. Tubes were microcentrifuged at high speed at 4° C. for 20 minutes. Supernatants were decanted, and the pellets were washed once with 70% ethanol. The pellets were allowed to dry at room temperature and then resuspended in TE (10 mM Tris-HCl, 1 mM EDTA, pH 7.4). Possible contaminating DNA was removed by incubating the RNA sample in 10 mM $MgCl_2$, 1 mM DTT and 5 U/ml RNase-free DNase (Boehringer-Mannheim) for 15 minutes at 37° C. The solution was adjusted to 10 mM Tris, 10 mM EDTA, 0.5% SDS and 1 mg/ml Pronase (Boehringer-Mannheim), followed by incubation at 37° C. for 30 minutes. Samples were extracted once with phenol-chloroform and once with chloroform; RNA was again precipitated in isopropanol at −20° C. Following centrifugation, the pellets were washed with 70% ethanol, then air dried and resuspended in sterile water. Total RNA was quantitated by measuring the optical density (OD) at 260 and 280 nm. The OD 260/280 ratios were typically 1.65–2.0. The RNA was stored at −70° C.

Poly $A^+$ RNA was isolated either from total RNA using an OLIGOTEX™ poly $A^+$ purification kit (Qiagen), or directly from tissue culture cells using the Messenger RNA Isolation kit (Stratagene) as per the manufacturer's protocols. If desired, alternative, conventional methods can be used to prepare poly $A^+$ RNA.

Production of in vitro Transcribed RNA

The 1.9 kb EcoRI fragment of chicken ovalbumin cDNA in pUC18 (McReynolds et al., 1978, Nature 273:723) containing the coding region and 3' untranslated region, was cloned into the EcoRI site of pGEM4Z (Promega). Clones containing the insert in both the sense and antisense orientations were isolated, and large scale plasmid preps were made using Maxi Prep Kits TM plasmid preparation kit (Qiagen). Plasmids were linearized with BamHI for use as templates for in vitro transcription. Transcription was carried out at 37° C. for 3–4 hours using the MEGAscript In Vitro Transcription Kit TM (Ambion) according to the manufacturer's protocol and adjusting the GTP concentration to 1.5 mM and including 6 mM $m^7G(5^1)ppp(5^1)G$ cap analog (Ambion). Other, conventional in vitro transcription methods also are suitable. Template DNA was digested with RNase-free DNase 1, and RNA was recovered by phenol:chloroform and chloroform extraction, followed by isopropanol precipitation. RNA was pelleted by microcentrifugation, and the pellet was washed once with 70% ethanol. The pellet was air-dried and resuspended in sterile water.

RNA was incubated for 30 minutes at 30° C. in 20 mM Tris-HCl, pH 7.0, 50 mM KCl, 0.7 mM $MnCl_2$, 0.2 mM EDTA, 100 μg/ml acetylated BSA, 10% glycerol, 1 mM ATP and 5000 U/ml yeast poly (A) polymerase (United States Biochemical). The capped, polyadenylated RNA was recovered by phenol:chloroform and chloroform extraction followed by isopropanol precipitation. RNA was pelleted by microcentrifugation, and the pellet was washed once with 70% ethanol. The pellet was air-dried and resuspended in sterile water. RNA was quantitated by measuring the OD at 260 and 280 nm, and the RNA stored at −70° C.

Oligodeoxynucleotide Directed Cleavage of OVA mRNA by RNase H

The procedure used for RNase H site-specific cleavage of ovalbumin mRNA was adapted from those previously described (Donis-Keller, 1979, Nucl. Acid. Res. 7: 179–192). Briefly, 5–10 μg mRNA from E.G7-OVA cells was suspended in 20 mM HEPES-KOH, pH 8.0, 50 mM KCl, 4 mM $MgCl_2$, 1 mM DTT, 50 μg/ml BSA and 2 μM of either the oligodeoxynucleotide 5'-CAG TTT TTC AAA GTT GAT TAT ACT-3' (SEQ ID NO: 5), which hybridizes to sequence in OVA mRNA that codes for the CTL epitope SIINFEKL (SEQ ID NO: 6), or 5'-TCA TAT TAG TTG AAA CTT TTT GAC-3' (SEQ ID NO: 7) (Oligos, etc.), which serves as a negative control. The samples were heated to 50° C. for 3 minutes followed by incubation at 37° C. for 30 minutes. RNase H (Boehringer-Mannheim) was added at 10 U/ml, and digestion proceeded for 30 minutes at 37° C. RNA was recovered by phenol:choloroform and chloroform extraction, followed by isopropanol precipitation. RNA was pelleted by microcentrifugation, and the pellet was washed once with 70% ethanol. The pellet then was air-dried and resuspended in sterile water. Cleavage of OVA mRNA was confirmed by oligo dT primed reverse transcription of test and control samples, followed by PCR with OVA specific primers that flank the cleavage site. PCR with actin-specific primers was used to control between test and control samples.

Pulsing of APC

APC were washed twice in Opti-MEM medium (GIBCO, Grand Island, N.Y.). Cells were resuspended in Opti-MEM medium at $2-5\times10^6$ cells/ml, and added to 15 ml polypropylene tubes (Falcon). The cationic lipid DOTAP (Boehringer Mannheim Biochemicals, Indianapolis, Ind.) was used to deliver RNA into cells (Walker et al., 1992, Proc. Natl. Acad. Sci. USA 89: 7915–7918). RNA (in 250–500 µl Opti-MEM medium) and DOTAP (in 250–500 µl Opti-MEM medium) was mixed in a 12×75 mm polystyrene tube at room temperature (RT) for 20 minutes. The RNA to DOTAP ratio routinely used was 1:2, and varied in certain experiments between 2:1 to 1:2. The complex was added to the APC ($2-5\times10^6$ cells) in a total volume of 2 ml and incubated at 37° C. in a water-bath with occasional agitation for 2 hours. The cells were washed and used as stimulators for primary CTL induction in vitro.

The synthetic peptide encoding the CTL epitope in chicken ovalbumin OVA, aa 257–264 SIINFEKL (H-2K$^b$ (SEQ ID NO: 6), was used for peptide pulsing. The peptide had unblocked (free) amino and caboxyl ends (Research Genetics, Birmingham, Ala.). Peptides were dissolved in serum-free IMDM and stored a −20° C.

Induction of CTL in vitro

T cells ($5\times10^6$ cells/ml) and RNA or peptide pulsed APC ($2.5\times10^5$ cells/ml) were cultured in IMDM with 10% FCS, 1 mM sodium pyruvate, 100 IU/ml penicillin, 100 mg/ml streptomycin, and $5\times10^{-5}$ M β-mercaptoethanol in 96 well U-bottom plates to give an R/S ratio of 20:1. After 5 days, cells were used as effectors in a standard 4 hours europium release assay.

Cytotoxicity Assay

In these assays, $5-10\times10^6$ target cells were labeled with europium diethylenetriamine pentaacetate for 20 minutes at 4° C. After several washes, $10^4$ europium-labeled targets and serial dilutions of effector cells at effector:target ratios of 50:1 to 6.25:1 were incubated in 200 µl of RPMI 1640 with 10½ heat-inactivated FCS in 96-well V-bottom plates. The plates were centrifuged at 500 g for 3 minutes and incubated at 37° C. and 5% $CO_2$ for 4 hours. 50 µl of the supernatant was harvested, and europium release was measured by time resolved fluorescence (Delta fluorometer, Wallace Inc., Gaithersburg, Md.). Spontaneous release was less than 25%. Standard errors (SE) of the means of triplicate cultures was less than 5%.

Immunotherapy

E.G7-OVA model: C57BL/6 mice were immunized once with irradiated, RNA-pulsed APC ($2\times10^6$ cells/mouse) or $5\times10^6$ E.G7-OVA or EL4 cells. At 10–14 days postimmunization, mice were challenged with $2\times10^7$ live E.G7-OVA cells injected subcutaneously in the flank region. Mice were monitored on a regular basis for tumor growth and size. Mice with tumor sizes >3.5 cm were sacrificed. All survivors were sacrificed at 40 days post-challenge.

F10.9-B16 melanoma model: Mice were received by intrafootpad injection $2\times10^5$ F10.9 cells. The postsurgical protocol was essentially as described previously (Porgador er al., 1995, Cancer Res. 55: 4941–4949). The legs of the mice were amputated when the local tumor in the footpad was 5.5–7.5 mm in diameter. Postamputation mortality was less than 5%. At two days postamputation, the mice were immunized intraperitoneally, followed by weekly vaccinations twice, for a total of three vaccinations. The mice were sacrificed based on the metastatic death in the non-immunized or control groups (at 28–32 days post-amputation). The metastatic loads were assayed by weighing the lungs and by counting the number of metastatic nodules.

Induction of a Primary CTL Response in vitro Using Dendritic Cells Transfected with Chicken Ovalbumin RNA The ability of RNA pulsed splenic dendritic cells (DC) derived from C57BL/6 (H-2K$^b$) mice to induce a primary CTL response in vitro was demonstrated in the E.G7-OVA tumor system. E.C-7-OVA cells were derived from the EL4 tumor cell line (H-2K$^b$ haplotype) by transfection with the chicken ovalbumin cDNA (Moore et al., 1988, Cell 54: 777–785). The chicken ovalbumin encodes a single dominant epitope (aa 257–264) in C57BL/6 mice (Rotzschke et al., 1991, Euro. Journal Immunology, 21: 2891–2891).

Dendritic cells pulsed with the OVA peptide (aa 257–264) incubated with T cells from naive mice induce a potent CTL response in vitro (FIG. 1). This example demonstrates that RNA can be used as a source of antigen to sensitize DC to present antigen to $CD8^-$ T cells. Splenic DC were isolated from C57BL/6 mice and pulsed with OVA peptide or incubated with RNA synthesized in vitro (OVA IVT RNA) from a plasmid encoding the chicken ovalbumin cDNA, and used to stimulate an OVA-specific primary CTL response in vitro. As shown in FIG. 1, both OVA peptide as well as OVA IVT RNA pulsed DC were capable of inducing an OVA specific primary CTL response (FIG. 1). RNA pulsed DC were consistently more effective stimulators than peptide pulsed DC. To test whether RNA isolated from E.G7-OVA cells was capable of sensitizing DC to stimulated primary, OVA-specific, CTL response, total RNA or poly $A^+$ RNA was isolated from E.G7-OVA or EL4 cells and incubated with DC. As shown in FIG. 1, DC pulsed with either total or poly $A^+$ RNA from E.G7-OVA cells but not from EL4 cells, were capable of inducing a strong OVA specific CTL response. Surprisingly, DC pulsed with unfractionated RNA, total or poly $A^+$, were as potent inducers of a primary CTL response as DC pulsed with the OVA peptide encoding a defined CTL epitope. Stimulation of a CTL response by (total or poly $A^+$) EL4 RNA pulsed DC was only marginally above background and statistically not significant (compare to lysis of EL4 targets by CTL stimulated with OVA peptide or OVA IVT RNA pulsed DC), reflecting the immunodominance of the OVA epitope and the relative weakness of the EL4 encoded antigens.

Figure 2:
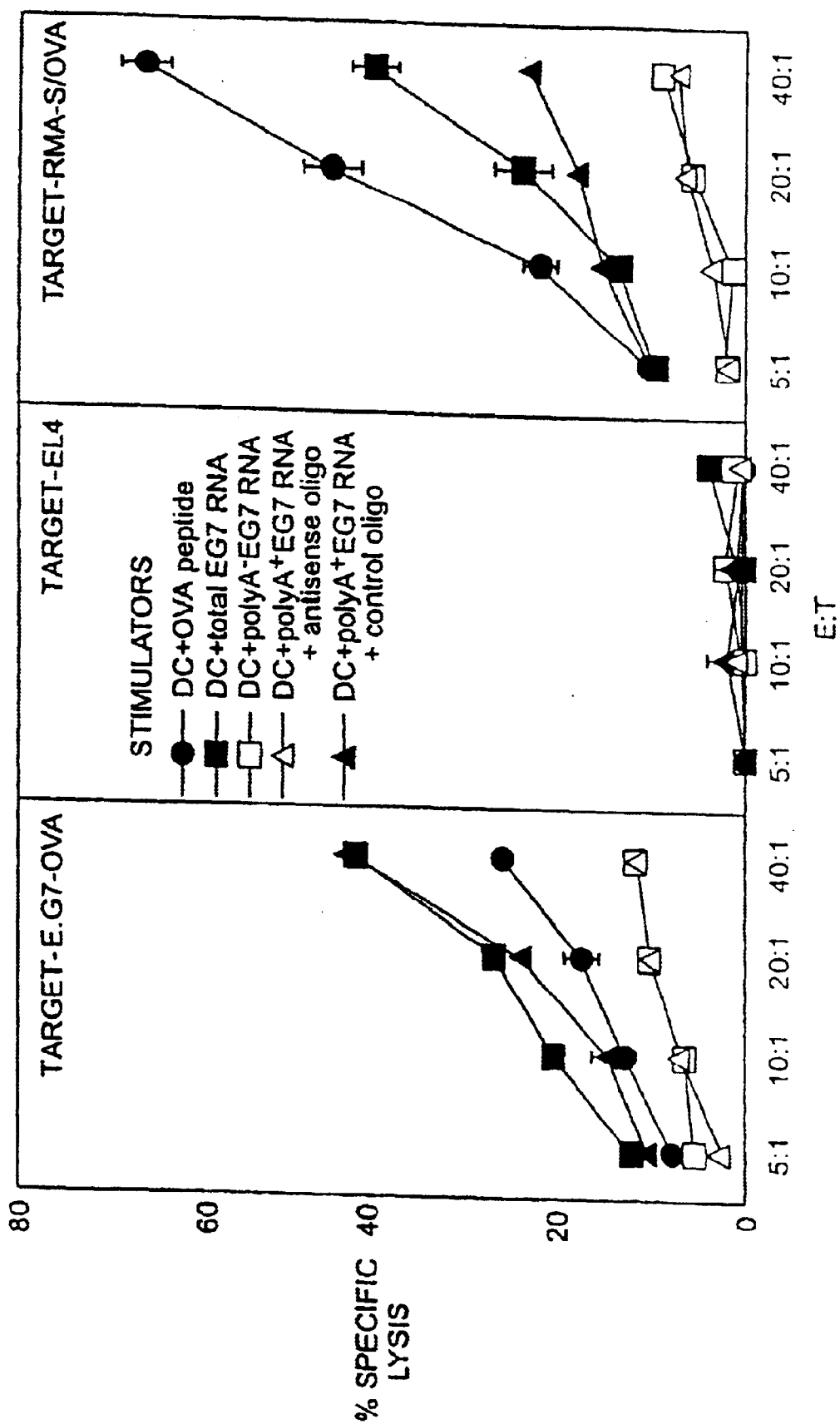
FIG. 2 is a graph illustrating that the sensitization of E.G7-OVA RNA pulsed DC for stimulation of OVA-specific primary CTL responses is mediated by the poly $A^+$ fraction of RNA. DC were pulsed with total RNA, poly $A^-$ RNA or poly $A^+$ RNA, and cultured with naive T cells in 96-well U-bottom. plates for 5 days. The poly A+ RNA fraction from E.G-7-OVA cells was treated with an antisense oligonucleotide specific for the CTL epitope encoding region of the OVA gene, or a control oligonucleotide followed by RNase H treatment to eliminate the hybridized RNA. DC pulsed with OVA peptide was used as a control. E.G7-OVA, EL4, and RMA cells pulsed with the OVA peptide were used as targets.

As is illustrated by FIG. 2, total, as well as poly $A^+$, but not poly $A^-$, RNA isolated from E.G7-OVA cells is capable of sensitizing DC to stimulate a primary CTL response. To prove that sensitization of DC is indeed mediated by RNA, poly $A^+$ RNA from E.G7-OVA cells was incubated with either an antisense oligonucleotide spanning the sequence encoding the single CTL epitope present in the chicken ovalbumin gene or with a control oligodeoxynucleotide, and then treated with RNase H to remove any RNA sequence to which the oligodeoxynucleotide probe has hybridized. As shown in FIG. 2, induction of a primary, OVA-specific CTL response was abolished when the poly $A^+$ RNA was incubated with the antisense, but not with the control, oligodeoxynucleotide. FIG. 2 also shows that cells expressing the complete ovalbumin gene, E.G7-OVA cells, and RMA-S cells pulsed with the 8 amino acid long OVA peptide encoding the single dominant CTL epitope are lysed to a similar extent following stimulation with total or poly $A^+$ E.G7-OVA RNA pulsed DC. This indicates, therefore, that the majority of epitopes presented by E.G7-OVA RNA pulsed DC correspond to the previously defined single dominant CTL epitope encoded in the chicken ovalbumin gene.

Induction of Anti-tumor Immunity by DC Pulsed with Tumor RNA

Figure 3:
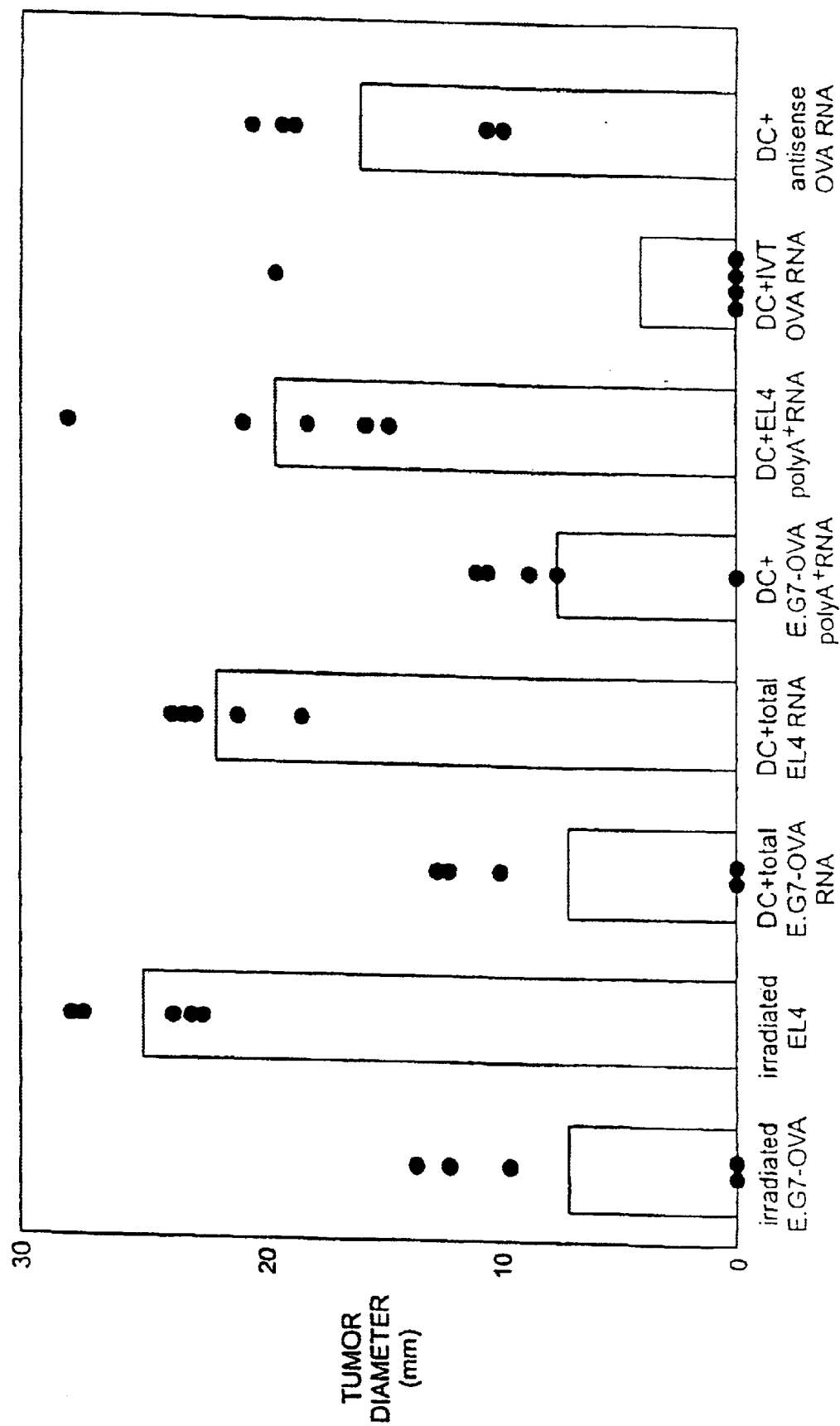
FIG. 3 is a histogram depicting the induction of anti-tumor immunity in vivo in mice following a single immunization with DC pulsed with RNA. DC were pulsed with either total or poly $A^+$ RNA from E.G7-OVA cells or EL4 cells, or with in vitro transcribed OVA RNA or control antisense OVA RNA. Mice were immunized with $2 \times 10^6$ DC or $5 \times 10^6$ irradiated E.G7-OVA or EL4 cells injected intraperitoneally, followed by a challenge with $2 \times 10^7$ live E.G7-OVA cells. Mice were periodically examined for tumor growth, and were sacrificed when the tumor diameter reached 3–4 cm. All mice were sacrificed at 35–40 days post-challenge.

This example demonstrates that vaccination of mice with OVA RNA pulsed DC provided protection against a challenge with E.G7-OVA tumor cells. Mice were immunized once with 2×10⁶ RNA pulsed DC or with 5×10⁶ irradiated E.G7-OVA cells. Ten days later, mice were challenged with a tumorigenic dose of E.G7-OVA cells. Appearance and size of the tumor were determined on a regular basis. FIG. 3 shows the size of the tumors at 37 days post-tumor implantation. The average tumor size in mice immunized with irradiated EL4 cells was 25 cm, while the average tumor size in animals immunized with the OVA expressing EL4 cells (E.G7-OVA) was only 7.03 cm. This difference is a reflection of the high immunogenicty of the chicken OVA antigen expressed in EL4 cells and the poor immunogenicity of the parental, EL4, tumor cell line. Vaccination with DC pulsed with RNA (total or poly A$^+$ fraction) derived from E.G7-OVA cells was as effective as vaccination with the highly immunogenic E.G7-OVA cells (average tumor size 7 cm). Vaccination with DC incubated with total or poly A$^-$ RNA derived from EL4 tumor cells had a slight protective effect (average tumor size: 22 cm and 19.5 cm, respectively) which was not statistically significant, consistent with poor to undetectable immunogenicity of EL4-derived antigens. Consistent with the primary CTL induction data (FIG. 1), vaccination of mice with OVA IVT RNA pulsed DC provided the most effective anti-tumor response (average tumor size: 3.9 cm), while vaccination with the control antisense OVA IVT RNA did not elicit a significant protective response.

The potency of DC pulsed with tumor-derived RNA was further evaluated in the B16/F10.9 (H-2$^b$) melanoma metastasis model. The B16/F10.9 melanoma tumor is poorly immunogenic, expresses low levels of MHC class I molecules, and is highly metastatic in both experimental and spontaneous metastasis assay systems (Porgador et al., 1996, J. Immunology 156: 1772–1780). Porgador et al. have shown that, when vaccinations are carried out after the removal of the primary tumor implant, only irradiated tumor cells transduced with both the IL-2 and the H-2K$^b$ genes, are capable of significantly impacting the metastatic spread of B16/F10.9 tumor cells in the lung (Porgador et al. 1995, Cancer Research 55: 4941–4949). Thus, the B16/F10.9 melanoma model and the experimental design used by Porgador et al. constitutes a stringent and clinically relevant experimental system to assess the efficacy of adjuvant treatments for metastatic cancer.

Figure 4:
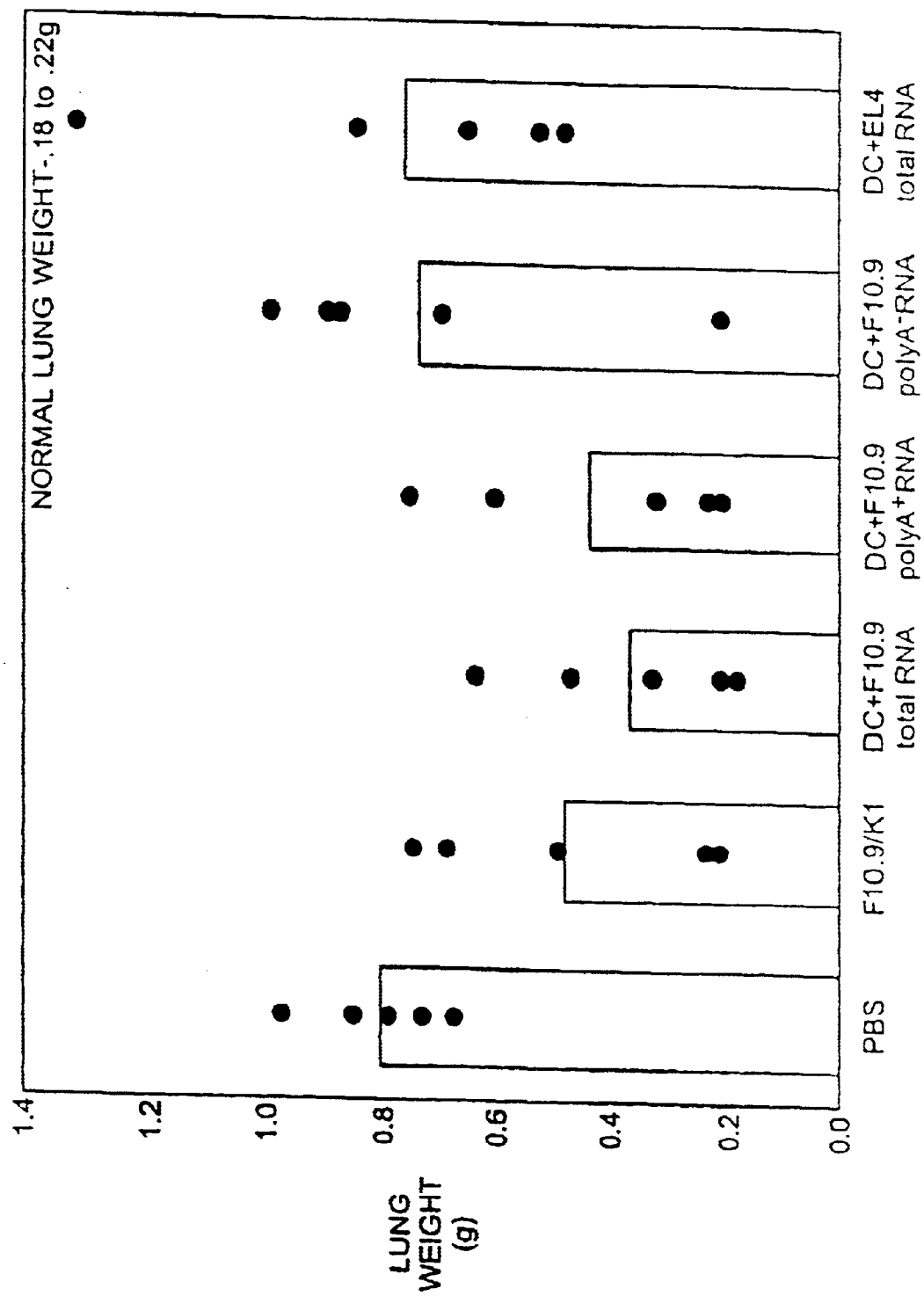
FIG. 4 is a histogram depicting the regression of spontaneous metastasis in mice vaccinated with DC pulsed with poly A+ RNA or total RNA in the B16-F10.9 melanoma model. Mice received by intrafootpad injection live F10.9 cells, and the legs were amputated when the tumor diameter reached 5.5–7.5 mm. Vaccinations were initiated 2 days post-amputation, and were followed by two more vaccinations at weekly intervals. Mice were vaccinated intraperitoneally with $2 \times 10^6$ total, poly A- or poly A- RNA pulsed DC, or irradiated F10.9 cells or F10.9/K1 cells, or PBS (as a control). Mice were sacrificed based on the metastatic death in the non-immunized or control groups (28–32 days post-amputation). Metastatic loads were assayed by weighing the lungs and by counting the number of metastatic nodules.

To demonstrate that immunization with tumor RNA pulsed DC, in accordance with the invention, was capable of causing the regression of preexisting lung metastases, primary tumors were induced by implantation of B16/F10.9 tumor cells in the footpad. When the footpad reached 5.5–7.5 mm in diameter, the tumors were surgically removed. Two days later, mice were immunized with irradiated B16/F10.9 cells, irradiated B16/F10.9 cells transduced with the H-2K$^b$ gene (F10.9K1), or with RNA pulsed DC preparations (FIG. 4). The mice received a total of three vaccinations given at weekly intervals. The average lung weight of a normal mouse is 0.18–0.22 g. Mice treated with PBS (a negative control) were overwhelmed with metastases. The mean lung weight of mice in this treatment group was 0.81 g; approximately three-quarters of the weight was contributed by the metastases, which were too many to count (>100 nodules). A similar me astatic load was seen when mice were treated with irradiated B16/F10.9 cells (data not shown), which confirms numerous previous observations that treatment with irradiated B16/F10.9 tumor cells alone has therapeutic benefit in this tumor model. As also previously shown, immunization with H-2K$^b$ expressing B16/F10.9 cells (F10.9K1, as a positive control) had a modest therapeutic benefit, as indicated by a statistically significant decrease in the average lung weight of the animals in this treatment group. A dramatic response, however, was seen in animals treated with DC that were pulsed with total RNA derived from 10.9 cells in accordance with the invention. The mean lung weight of mice in this treatment group was 0.37 g. A significant dramatic response also was seen in mice treated with DC pulsed with poly A$^+$ RNA derived from F10.9 cells in accordance with the invention (average lung weight: 0.42 g). By contrast, no statistically significant decrease in metastatic load was seen in mice treated with DC that were pulsed with either the poly A$^-$ RNA fraction derived from F10.9 cells or with total RNA isolated from EL4 tumor cells.

The observation that cells expressing the OVA protein (E.G7-OVA) or cells pulsed with the OVA peptide were efficiently lysed by CTL, and the sensitization of DC fractionated with poly A$^+$ RNA, strongly suggest that RNA-mediated stimulation of CTL occurs via translation of the input RNA and generation of the predicted class I restricted epitopes, in this case a single dominant epitope encoded in the chicken OVA peptide. These data show that RNA mediated sensitization of DC is more effective than pulsing with peptide because the transfected RNA can serve as a continuous source for the production of antigenic peptides.

EXAMPLE 2

The following experimental details are relevant to the studies described below.

Cell Lines

An autologous tumor cell line was established from resected retroperitoneal lymph node metastasis from a primary colon adenocarcinoma. Tumor tissue was mechanically disrupted and propagated in matrigel basement membrane matrix (Becton Dickinson, Bedford, Mass.) in RPMI supplemented with 10% FCS, 2 mM L-glutamine, 100 μg/ml streptomycin and 100 U/ml penicillin (complete RPMI). Cells propagated as non-adherent clusters with looped structure. Resemblance with glandular formation was confirmed with hematoxyline-eosin staining of a frozen section of the cluster. Clusters were eventually transferred to medium without matrigel to form a suspension cell line. Immunohistochemical analysis determined that the tumor cells were PAS+, CEA+, A33+, Ki-67+, PCNA+ (proliferating cell nuclear antigen) and p53+. Autologous tumor cells were maintained DMEM-F12 supplemented with 10% FCS, 25 mM HEPES, 2 mM L-glutamine, 1 μg/ml insulin and 1 mM sodium pyruvate.

Precursor-derived DC

Blood samples were obtained from the patient, and PBMC were isolated over a ficoll hypaque density gradient. DC were generated from PBMC in the presence of GM-CSF and IL-4 as described by Romani et al (J. Exp. Med. 180:83–93 (1994)) with minor modifications in the absence of serum (Morse et al, Annals of Surgery 226:6–16 (1997)). DC were cryopreserved in 90% autologous plasma+10% DMSO at 5×10⁶/ml and PBMC to be used as responders were cryopreserved at 5 10⁷/ml.

Isolation of Autologous Tumor Total Cellular RNA

Total RNA was isolated from autologous tumor cells using RNeasy RNA isolation kits (Qiagen, Santa Clarita, Calif., USA) according to the manufacturer's protocol.

Production of in vitro Transcribed (IVT) Carcinoembryonic Antigen (CEA) RNA

CEA cDNA in pGEM3Zf+ plasmid was linearized with HindIII for use as templates for in vitro transcription. RNA was made and polyadenylated as described in Boczkowski et al (J. Exp. Med. 184:465–472 (1996)).

Transfecting DC with RNA

DC ($5 \times 10^6$ cells/ml) in AIM V medium were pulsed with CEA RNA (2 μg) or autologous tumor RNA (10 μg).

Induction of Primary CTL Response in vitro

Stimulation of PBMC and expansion of CTL was done as described in Wong et al (J. Immunotherapy 21:32–40 (1998)). Briefly, autologous PBMC were cocultured with antigen-pulsed DC with IL-7 and IL-2. CD8+ T cells were isolated using Dynabeads M-450 CD8 followed by DETACHaBEAD CD8 to obtain purified, phenotypically and functionally unaltered cells (Dynal Inc., Lake Success, N.Y.). The purity of CD8− T cells was >90% by FACS analysis. The captured CD8+ T cells were cultured in RPMI 1640 and 10% FCS and 20 U/ml of IL-2 at 37° C. Two days post-purification T cell blasts were restimulated with antigen-pulsed DC. CTL assays were done 5 days post-restimulation. A standard europium release CTL assay was performed and europium release was measured by time resolved fluorescence (Volgmann et al, J. Immunol. Methods 119:45–51 (1989)). Specific cytotoxic activity was determined using the formula: % specific release=[(experimental release−spontaneous release)/(total release−spontaneous release)]×100. Spontaneous release was less than 25% of total release by detergent in all assays. Standard errors of are means of triplicate cultures was less than 5%.

The Ability of CEA-specific CTL to Recognize and Lyse Autologous Tumor Cells

Autologous DC were generated in serum-free AIM-V media as described by Morse et al (Ann. Surg. 226:6–16 (1997)) and transfected with "naked" RNA from a variety of sources: 1) in vitro transcribed (IVT) CEA RNA, 2) total tumor RNA from autologous CEA+ tumor (notwithstanding the fact that the CEA mRNA species represents a minority of the cellular RNA pool), 3) control IVT RNA encoding an irrelevant protein, green fluorescent protein (GEP) (Chalfie et al, Science 263:802–805 (1994)), or 4) control total cellular RNA from Epstein-Barr virus transformed B cell lines (BLCL). The RNA transfected DC were used both to stimulate antigen-specific CTL in vitro as described above, and used as target cells in cytotoxicity assays.

Figure 5:
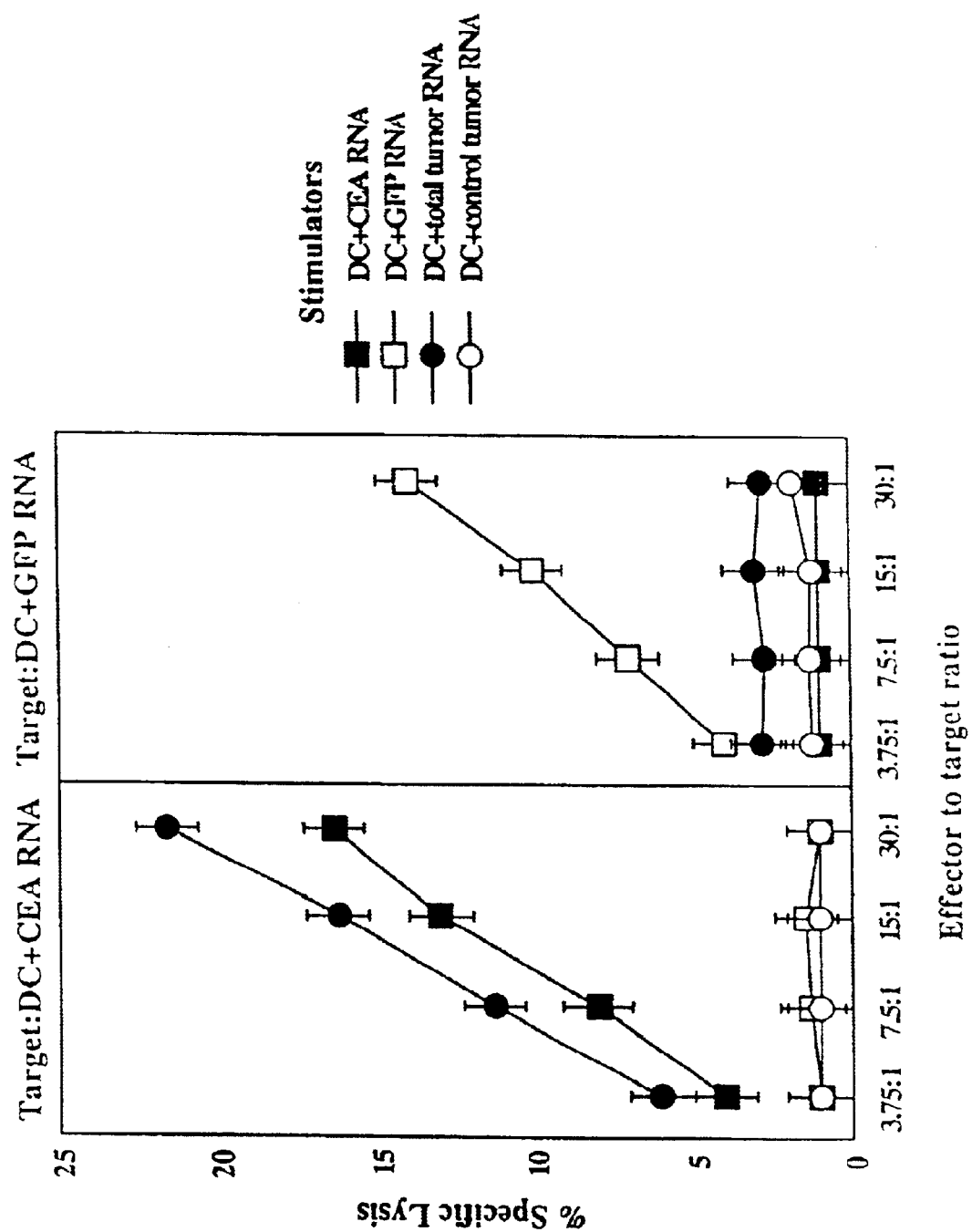
FIG. 5 shows the induction of CEA-specific CTL response in vitro using DC transfected with in vitro transcribed (IVT) CEA RNA or total tumor RNA from autologous CEA+ tumor. DC were generated in serum-free AIM-V media and transfected with "naked" RNA from: 1) in vitro transcribed (IVT) CEA RNA, 2) control IVT RNA encoding an irrelevant protein, GFP, 3) total tumor RNA from autologous CEA+ tumor, or 4) control total cellular RNA from Ebstein-Barr virus transformed B cell lines (BLCL). PBMC from the patient were stimulated in vitro with the transfected DC as described in Example 2. Induction of CEA-specific CTL was measured using as targets DC transfected with CEA RNA or GFP RNA (control targets).

It was first attempted to demonstrate the generation of CEA-specific CTL in vitro. DC were transfected with either IVT CEA RNA, or total autologous tumor RNA and stimulated PBMC in vitro to generate either CEA-specific or tumor-specific CTL. The ability of CTL to recognize tumor antigens was first determined by standard cytotoxicity assays using autologous, RNA-transfected DC as targets. As shown in FIG. 5, CEA-specific CTL were able to recognize and lyse CEA RNA, but not GFP RNA transfected DC. Remarkably, tumor-specific CTL were as comparable in recognizing and lysing CEA-expressing targets cells as the CEA-specific CTL, indicating that the levels of CEA RNA in the total tumor RNA pool were sufficient to stimulate CEA-specific CTL. Stimulation of PBMC with DC transfected with GEP RNA induced CTL capable of lysing GFP RNA transfected DC, but not CEA RNA transfected targets.

Figure 6:
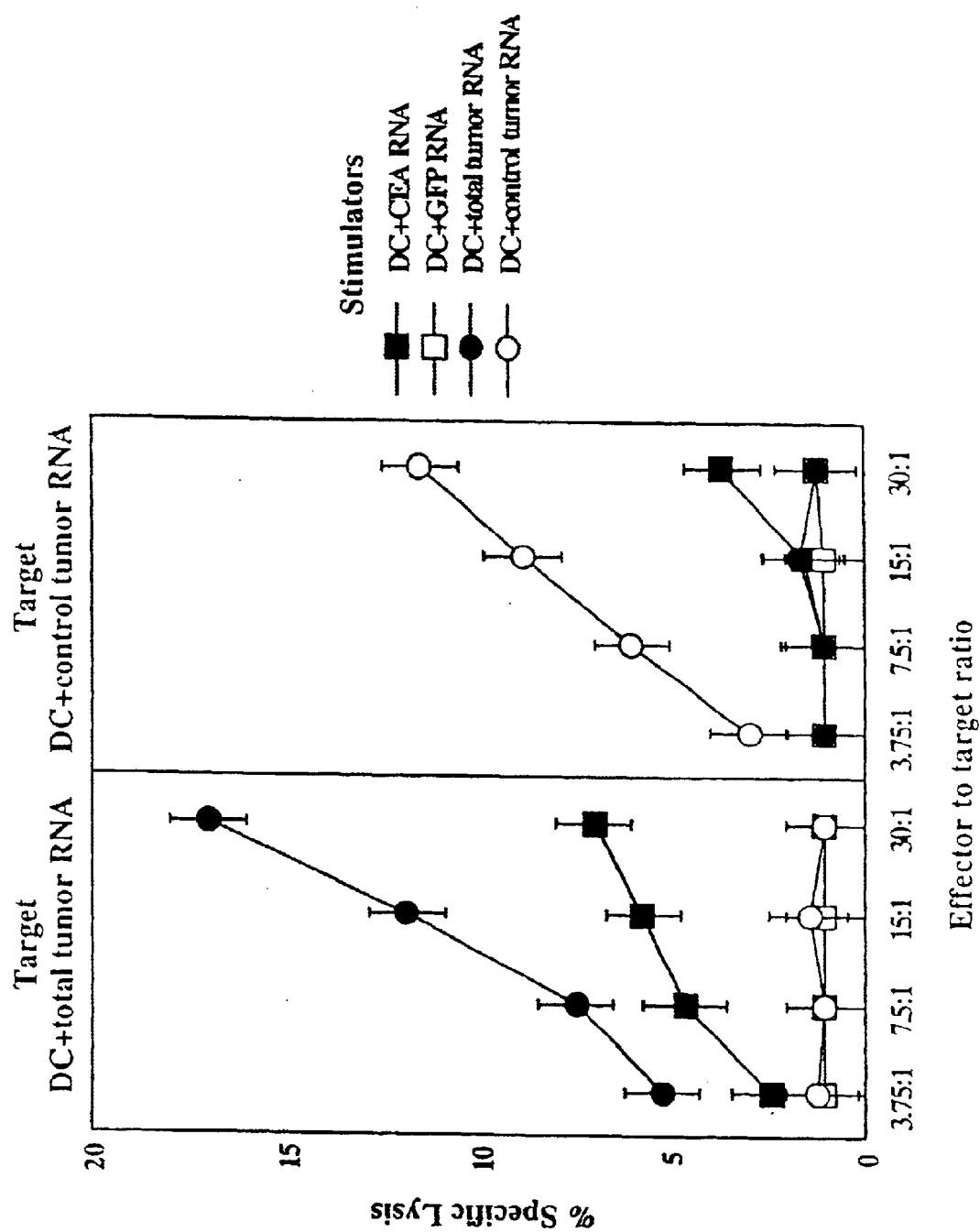
FIG. 6 shows the induction of tumor-specific CTL response in vitro using DC transfected with in vitro transcribed (IVT) CEA RNA or total tumor RNA from autologous CEA+ tumor. DC were generated in serum-free AIM-V media and transfected with "naked" RNA from: 1) in vitro transcribed (IVT) CEA RNA, 2) control IVT RNA encoding an irrelevant protein, GFP, 3) total tumor RNA from autologous CEA+ tumor, or 4) control total cellular RNA from Epstein-Barr virus transformed B cell lines (BLCL). PBMC from the patient were stimulated in vitro with the transfected DC as described in Example 2. Induction of CEA-specific CTL was measured using as targets DC transfected with CEA RNA or GFP RNA (control targets).

It was next attempted to demonstrate that the CEA-specific CTL and tumor-specific CTL could recognize and lyse tumor antigens encoded by autologous tumor. As shown in FIG. 6, both CEA-specific CTL and tumor-specific CTL lysed DC targets transfected with autologous CEA+ tumor RNA but not the control (BLCL) tumor RNA. The lysis appears to be specific for CEA as stimulation of PBMC with DC transfected with total RNA from a BLCL line (CEA−) induced CTL capable of lysing BLCL RNA transfected DC, but not autologous tumor RNA transfected targets. As predicted, DC transfected with GFP RNA did not induce tumor-specific CTL.

The levels of lysis obtained with the tumor specific CTL (PBMC stimulated with DC transfected with total tumor RNA) were significantly higher than the lysis obtained with CEA-specific CTL (PBMC stimulated with DC transfected with IVT CEA RNA). One possible explanation for the increased lysis is that the tumor cells express proteins in addition to CEA which serve as tumor antigens. Thus, unfractionated tumor RNA transfected DC elicits responses to a host of other, yet unidentified tumor antigens, whereas IVT CEA RNA transfected DC stimulate only CEA-specific responses.

Figure 7:
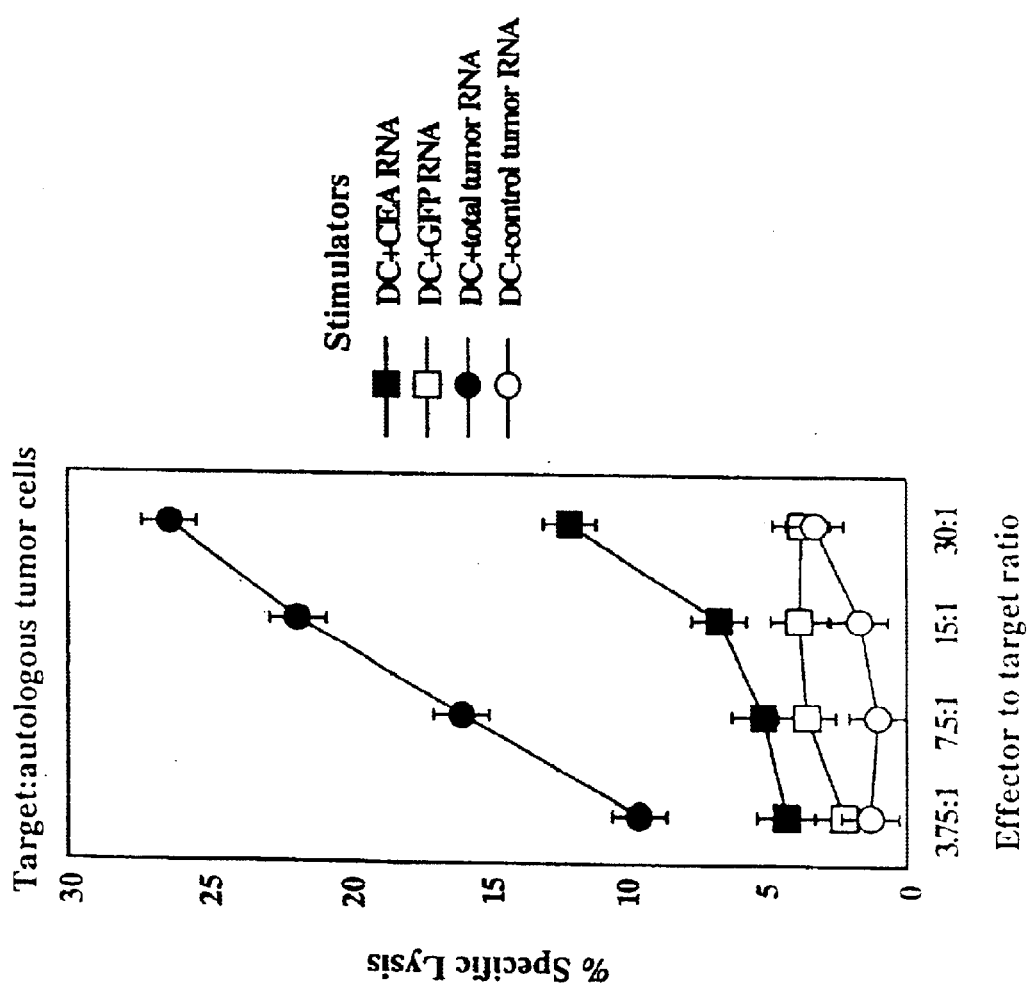
FIG. 7 shows DC transfected with in vitro transcribed (IVT) CEA RNA or total tumor RNA from autologous CEA+ tumor lyse autologous tumor cells. DC were generated in serum-free AIM-V media and transfected with "naked" RNA from: 1) in vitro transcribed (IVT) CEA RNA, 2) control IVT RNA encoding an irrelevant protein, GFP, 3) total tumor RNA from autologous CEA+tumor, or 4) control total cellular RNA from Ebstein-Barr virus transformed B cells lines (BLCL). PBMC from the patient were stimulated in vitro with the transfected DC and induction of CTL was measured using autologous tumor cells as targets.

It was further attempted to determine if CEA specific CTL or tumor-specific CTL were capable of recognizing and lysing autologous tumor cells, suggesting that the CTL generated in vitro by RNA transfected DC were high-avidity CTL capable of recognizing target antigens processed and presented in a more authentic context, i.e., by the tumor cells themselves. Therefore, CEA-specific CTL (PBMC stimulated with DC transfected with IVT CEA RNA) and tumor-specific CTL (PBMC stimulated with DC transfected with total tumor RNA) were used in cytotoxicity assays with autologous tumor cells as targets (FIG. 7). There was recognition and lysis of autologous tumor cells by both CEA-specific and tumor-specific CTL, but the levels of lysis obtained with tumor-specific CTL were significantly higher than the lysis obtained with CEA-specific CTL. This is again consistent with the expression of proteins within the tumor cells in addition to CEA which serve as tumor antigens. DC transfected with GFP RNA or total BLCL RNA did not lyse autologous tumor cells.

Figure 8:
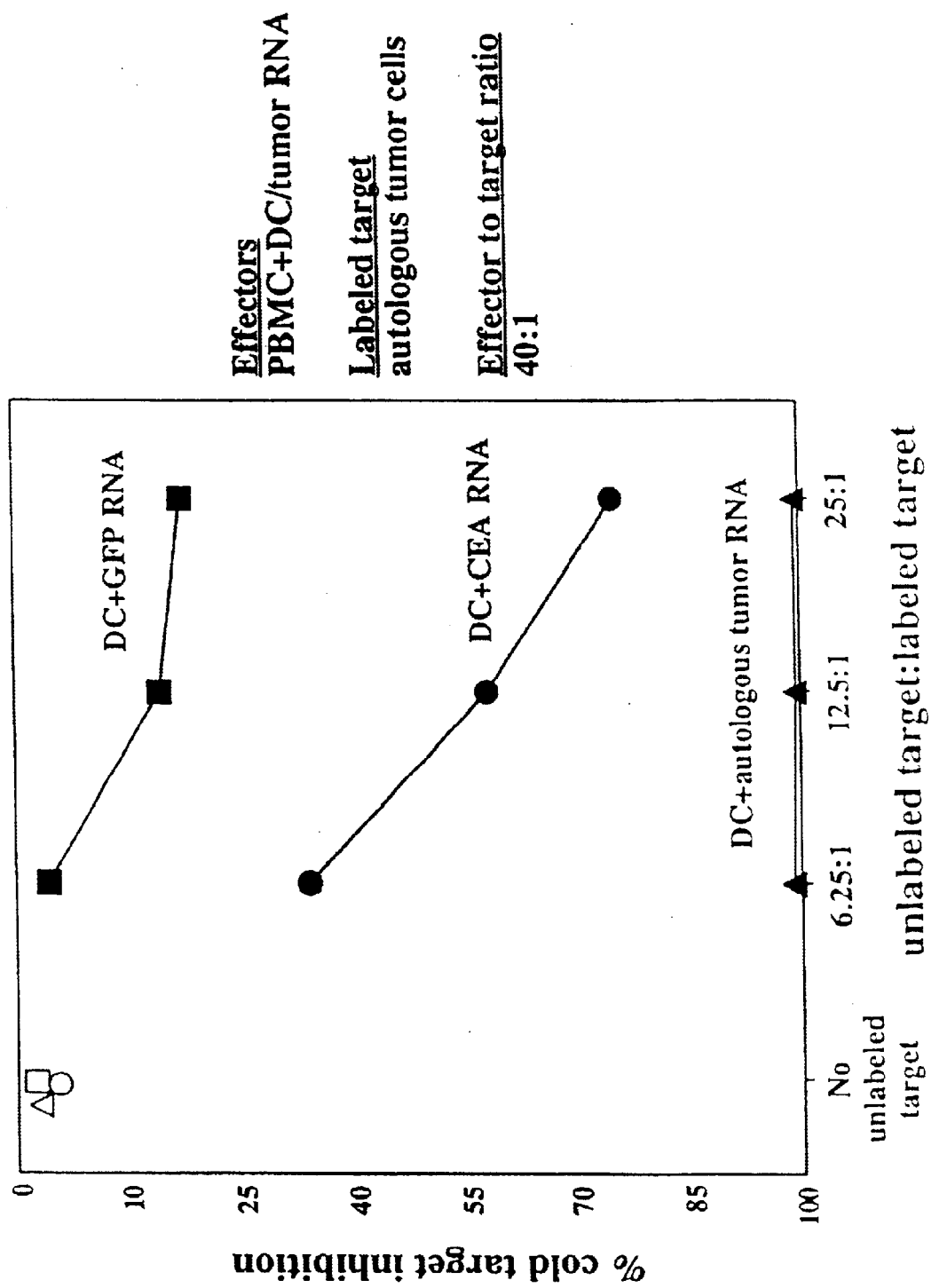
FIG. 8 shows CTL induction by DC transfected with autologous total tumor RNA: cold target inhibition. PBMC from the patient were stimulated in vitro with DC transfected with total tumor RNA from autologous CEA+tumor. Autologous tumor cells were used as the labeled targets, which were competed out using either DC transfected with either autologous tumor RNA, or with CEA RNA, or with GFP RNA at the varying ratios of unlabeled target to labeled target.

To demonstrate that tumor-specific CTL recognized not only CEA but other, yet unidentified antigens, cold target inhibition assays were performed. As shown in FIG. 8, tumor-specific CTL were generated from PBMC stimulated with DC transfected with total tumor RNA. Autologous tumor cells were used as the labeled targets, which were competed out using either DC transfected with autologous tumor RNA, DC transfected with CEA RNA, or DC transfected with GFP RNA. DC pulsed with total tumor RNA under non-saturating conditions of unlabeled to labeled target (6.25:1 and 12.5:1) completely blocked the CTL from lysing autologous tumor cells. DC transfected with CEA RNA caused a partial inhibition and DC transfected with GFP RNA did not inhibit the lysis of the autologous tumor cells. This experiment demonstrates that total tumor RNA transfected DC stimlate CTL to antigens other than CEA.

Therapeutic Use

The invention can be used to treat or prevent tumor formation in a patient (e.g., melanoma tumors, bladder tumors, breast cancer tumors, colon cancer tumors, prostate cancer tumors, and ovarian cancer tumors). Similarly, the invention can be used to treat or prevent infection in a patient with a pathogen such as a bacterium (e.g., Salmonella, Shigella, or Enterobacter) or a virus (e.g., a human immunodeficiency virus, a Herpes virus, an influenza virus, a poliomyelitis virus, a measles virus, a mumps virus, or a rubella virus).

In treating or preventing tumor formation or pathogen infection in a patient, it is not required that the cell(s) that is administered to the patient be derived from that patient. Thus, the antigen-presenting cell can be obtained from a matched donor, or from a culture of cells grown in vitro. Methods for matching haplotypes are known in the art. Similarly, it is not required that the RNA be derived from the patient to be treated. RNA from a donor can be used.

It is preferable that treatment begin before or at the onset of tumor formation or infection, and continue until the cancer or infection is ameliorated. However, as the examples described herein illustrate, the invention is suitable for use even after a tumor has formed, as the invention can cause a regression of the tumor. In treating a patient with a cell of vaccine produced according to the invention, the optimal dosage of the vaccine or cells depends on factors such as the weight of the mammal, the severity of the cancer or infection, and the strength of the CTL epitope. Generally, a dosage of $10^5$ to $10^8$ RNA-loaded antigen-presenting cells/kg body weight, preferably $10^6$ to $10^7$ cells/kg body weight, should be administered in a pharmaceutically acceptable excipient to the patient. The cells can be administered by using infusion techniques that are commonly used in cancer therapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

Where the antigen-presenting cell is used to induce a CTL response in vitro, the resulting effector CTLs can subsequently be administered to a mammal in a CTL-based method of therapy (see, e.g., PCT/US91/06441). CTL produced in vitro with the antigen-presenting cells of the invention can be administered in a pharmaceutically acceptable excipient to a mammal by employing conventional infusion methods (see, e.g., Rosenberg et al., supra). Typically, $10^9$–$10^{10}$ cells are administered over the course of 30 minutes, with treatment repeated as necessary. Such a CTL-based method of therapy may be combined with other methods, such as direct administration of the antigen-presenting cells of the invention. The CTL and antigen-presenting cells may be autologous or heterologous to the patient undergoing therapy. If desired, the treatment may also include administration of mitogens (e.g., phytohemagglutinin) or lymphokines (e.g., IL-2 or IL-4) to enhance CTL proliferation.

What is claimed is:

1. A method for detecting a T cell response against a tumor antigen comprising:
   i) isolating RNA from tumor cells,
   ii) introducing said RNA resulting from step (i) into antigen presenting cells (APCs) isolated from an individual to produce target cells that functionally present on the surface thereof an antigen encoded in said RNA,
   iii) contacting said target cells with T-cells from said individual, and
   iv) assaying:
      a) for cytotoxicity wherein lysis of said target cells indicates that said individual has T cells that recognize said tumor antigen, or
      b) for an increase in cytokine production by said T cells, relative to a level of cytokine production in T cells not contacted with said target cells, wherein an increase in cytokine production indicates that said individual has T cells that recognize said tumor antigen.

2. The method according to claim 1 wherein said RNA isolated in step (i) is amplified prior to step (ii).

3. The method according to claim 1 wherein said APCs are dendritic cells or macrophages.

4. The method according to claim 1 wherein said step (iv) comprises assaying for said cytotoxicity.

5. The method according to claim 1 wherein said step (iv) comprises assaying for said increase in cytokine production.

6. The method according to claim 1 wherein said T cells are CD8+ cells.

7. The method according to claim 1 wherein said T cells are CD4+ T cells.

8. A method for detecting a T cell response against a pathogen antigen comprising:
   i) isolating RNA from a pathogen,
   ii) introducing said RNA resulting from step (i) into antigen presenting cells (APCs) isolated from an individual to produce target cells that functionally present on the surface thereof an antigen encoded in said RNA,
   iii) contacting said target cells with T-cells from said individual, and
   iv) assaying:
      a) for cytotoxicity wherein lysis of said target cells indicates said individual has T cells that recognize said pathogen antigen, or
      b) for an increase in cytokine production by said T cells, relative to a level of cytokine production in T cells not contacted with said target cells, wherein an increase in cytokine production indicates that said individual has T cells that recognize said pathogen antigen.

9. The method according to claim 8 wherein said RNA isolated in step (i) is amplified prior to step (ii).

10. The method according to claim 8 wherein said APCs are dendritic cells or macrophages.

11. The method according to claim 8 wherein said step (iv) comprises assaying for said cytotoxicity.

12. The method according to claim 8 wherein said step (iv) comprises assaying for said increase in cytokine production.

13. The method according to claim 8 wherein said T cells are CD8+ cells.

14. The method according to claim 8 wherein said T cells are CD4+ T cells.

* * * * *